United States Patent [19]
Matsumoto et al.

[11] Patent Number: 5,202,312
[45] Date of Patent: Apr. 13, 1993

[54] IMIDAZOLE-CONTAINING PEPTIDES HAVING IMMUNOMODULATORY ACTIVITY

[75] Inventors: Kazuo Matsumoto, Ibaraki; Kimiaki Hayashi, Suita; Kenichi Nunami, Kobe; Tadashi Sato, Takatsuki; Isao Takata, Toyono, all of Japan

[73] Assignee: Tanabe Seiyaku Co., Ltd., Osaka, Japan

[21] Appl. No.: 444,315

[22] Filed: Dec. 1, 1989

[30] Foreign Application Priority Data

Dec. 7, 1988 [JP] Japan .................. 63-310867

[51] Int. Cl.$^5$ .................. A61K 37/02; C07K 5/08
[52] U.S. Cl. ...................... 514/18; 530/331
[58] Field of Search .................. 514/18; 530/331

[56] References Cited

U.S. PATENT DOCUMENTS 4,048,305 9/1977 Molteni et al. .
5,051,441 9/1991 Matsumoto et al. ............. 514/401

FOREIGN PATENT DOCUMENTS 0223437 5/1987 European Pat. Off. .
0231919 8/1987 European Pat. Off. .
2155470 9/1985 United Kingdom .

OTHER PUBLICATIONS

Mizel et al., Proc. Natl. Acad. Sci. USA, vol. 78, No. 4, pp. 2474–2477, 1981.
Nagai et al., Japan, J. Pharmacol., 32, 1117–1124 (1982).
Sochynsky et al., Pharma Projects, vol. 7, May 1986.
Gordon et al., Journal of Leukocyte Biology, vol. 42, pp. 197–203; (1987).

Primary Examiner—Merrell C. Cashion, Jr.
Assistant Examiner—S. G. Marshall
Attorney, Agent, or Firm—Birch, Stewart, Kolasch & Birch

[57] ABSTRACT

Imidazole-containing peptide of the formula:

$$R^1-CON-X^1-CON-X^2-CO-NH-A-\underset{N}{\underset{|}{\bigwedge}}\overset{NH}{\underset{R^7}{\bigvee}}R^6 \quad (I)$$

with substituents $R^2, R^3$ on first CH and $R^4, R^5$ on second CH.

wherein $R^1$ is a branched alkyl group, a branched alkyloxy group or an aryl-substituted lower alkyloxy group, $R^2$ and $R^4$ are the same or different and each is hydrogen atom or a lower alkyl group, $R^3$ and $R^5$ are a phenyl-substituted lower alkyl group, $R^6$ is hydrogen atom or a lower alkoxycarbonyl group, $R^7$ is hydrogen atom or a nitrogen-containing heterocyclic group-substituted lower alkylthio group, $X^1$ and $X^2$ are the same or different and each is $$-\overset{|}{C}H-,\ -\overset{|}{O}CH-\ \text{or}\ -\overset{|}{N}-,$$

A is a lower alkylene group which may be substituted with a substituent selected from the group consisting of a lower alkoxy group, hydroxymethyl group and a group of the formula:

$$-CON\overset{R^8}{\underset{R^9}{\diagdown}}$$

and $R^8$ and $R^9$ are the same or different and each is hydrogen atom or a lower group, or a pharmaceutically acceptable salt thereof, which is useful as an immunomodulator and as an agent for the treatment and/or prophylaxis of autoimmune diseases such as rheumatoid arthritis, multiple sclerosis, systemic lupus erthematodes, glomerulonephris, rhumatic fever or type I diabetes and atopic allergy, a processes for the preparation thereof, and a pharmaceutical composition containing said compound as an active ingredient.

7 Claims, No Drawings

IMIDAZOLE-CONTAINING PEPTIDES HAVING IMMUNOMODULATORY ACTIVITY

FIELD OF THE INVENTION

This invention relates to novel imidazole-containing peptides and processes for preparation thereof.

BACKGROUND OF THE INVENTION

It is known that N-acetyl-L-phenylalanyl-L-phenylalanyl-L-histidine methyl ester shows anti-gastric and anti-ulcer activity (U.S. Pat. No. 4,048,305).

SUMMARY OF THE INVENTION

As a result of various investigations, it has been unexpectedly found that, while the above known compound shows scarcely an immunomodulatory effect, the peptides which are obtained by replacing acetyl group of the known compound with a bulky group such as pivaloyl group, tert.-butyloxycarbonyl group or benzyloxycarbonyl group show potent immunomodulatory effect.

Thus, an object of the invention is to provide novel imidazole-containing peptide having excellent immunomodulatory effect. Another object of the invention is to provide processes for preparing said compounds. A further object of the invention is to provide a pharmaceutical composition suitable for the treatment and/or prophylaxis of autoimmune diseases. These and other objects and advantages of the invention will be apparent to those skilled in the art from the following description.

DETAILED DESCRIPTION OF THE INVENTION

This invention relates to imidazole-containing peptides of the formula:

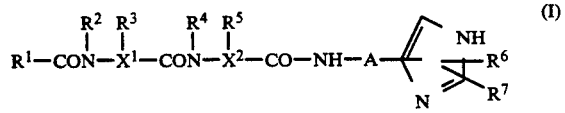

wherein $R^1$ is a branched alkyl group, a branched alkyloxy group or an aryl-substituted lower alkyloxy group, $R^2$ and $R^4$ are the same or different and each is hydrogen atom or a lower alkyl group, $R^3$ and $R^5$ are a phenyl-substituted lower alkyl group, $R^6$ is hydrogen atom or a lower alkoxycarbonyl group, $R^7$ is hydrogen atom or a nitrogen-containing heterocyclic group substituted lower alkylthio group, $X^1$ and $X^2$ are the same or different and each is

A is a lower alkylene group which may be substituted with a substituent selected from the group consisting of a lower alkoxycarbonyl group, hydroxymethyl group and a group of the formula:

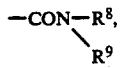

and $R^8$ and $R^9$ are the same or different and each is hydrogen atom or a lower group, or a pharmaceutically acceptable salt thereof.

The compound (I) of the invention or a salt thereof has a variety of excellent characteristics as an immunomodulator. For example, the compound (I) or a salt thereof shows potent macrophage migration enhancement activity in a macrophage migration assay which is used in measurement of cell-mediated immune activity. The compound (I) of the invention also shows a potent immunomodulatory effect such as inhibition of delayed type hypersensitivity. Further, the compound (I) or a pharmaceutically acceptable salt thereof has low toxicity and shows high safety.

Examples of the imidazole-containing peptide of the invention are those of the formula (I) wherein $R^1$ is branched alkyl group of 3 to 6 carbon atoms, branched alkyloxy group of 3 to 6 carbon atoms or phenyl-substituted alkoxy ($C_{1-4}$) group, and $R^7$ is hydrogen atom or a pyridyl-substituted alkylthio ($C_{1-4}$) group.

Other examples of the compound of the invention are those of the formula (I) wherein $R^2$ and $R^4$ are hydrogen atom or an alkyl group of 1 to 4 carbon atoms, $R^3$ and $R^5$ are phenyl-substituted alkyl ($C_{1-4}$) group, $R^6$ is an alkoxy ($C_{1-4}$)-carbonyl group, and A is an alkylene group of 1 to 4 carbon atoms, an alkoxy ($C_{1-4}$)carbonyl-substituted alkylene ($C_{1-4}$)group, hydroxymethyl substituted alkylene ($C_{1-4}$) group, a carbamoyl-substituted alkylene ($C_{1-4}$) group, N-monoalkyl ($C_{1-4}$)-carbamoyl-substituted alkylene ($C_{1-4}$) group, or N-di-alkyl($C_{1-4}$)-carbamoyl-substituted alkylene ($C_{1-4}$) group.

Preferred examples of the compound of the invention are those of the formula (I) wherein $R^1$ is tert.-butyl, tert.-butyloxy or benzyloxy, $R^2$ and $R^4$ are hydrogen atom or methyl, $R^3$ and $R^5$ are benzyl or phenethyl, $R^6$ is hydrogen atom or methoxycarbonyl, $R^7$ is hydrogen atom, 2-pyridylmethylthio or 3-pyridylmethylthio, and A is methylene, ethylene, methoxycarbonylethylene, hydroxymethylethylene or carbamoylethylene.

More preferred compounds of the invention are those of the formula (I) wherein $R^2$ and $R^4$ are hydrogen atom, and $R^3$ and $R^5$ are benzyl.

The imidazole-containing peptide (I) of the invention may exist in the form of tautometric isomers in the imidazole part as shown in the following formula:

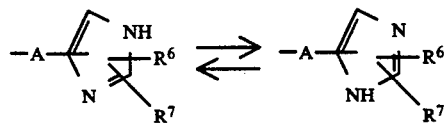

wherein the symbols are the same as defined above, and this invention includes these isomers.

Further, the imidazole-containing peptide (I) of the invention can exist in the form of optical isomers when the asymmetric carbon atom(s) is involved therein, and all of optical isomers or a mixture thereof are included within the scope of the invention. Among these isomers, however, the compound in which all of the asymmetric carbon atom(s) are (S)-configuration is more preferred for pharmaceutical use.

According to the invention, the imidazole-containing peptide (I) can be prepared by the step of:

(A) condensing a compound of the formula:

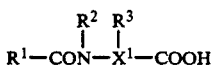 (II)

wherein the symbols are the same as defined above, a salt or a reactive derivative thereof with a compound of the formula:

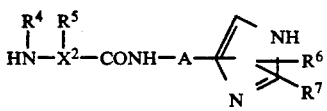 (III)

wherein the symbols are the same as defined above, or a salt thereof, or (B) condensing a compound of the formula:

 (IV)

wherein the symbols are the same as defined above, a salt or a reactive derivative thereof with a compound of the formula:

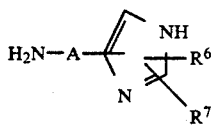 (V)

wherein the symbols are the same as defined above, or a salt thereof, or (C) condensing a compound of the formula:

$R^1COOH$ (VI)

wherein the symbols are the same as defined above, a salt or a reactive derivative thereof with a compound of the formula:

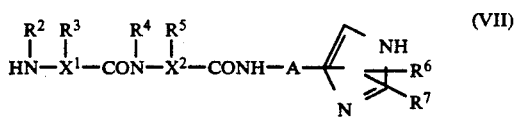 (VII)

wherein the symbols are the same as defined above, or a salt thereof.

Among the compound (I), a compound of the formula:

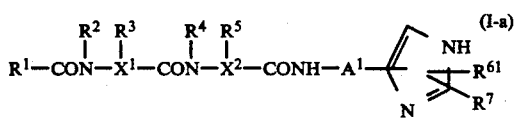 (I-a)

wherein $R^{61}$ is hydrogen atom, $A^1$ is hydroxymethyl-substituted lower alkylene group and $R^1$, $R^2$, $R^3$, $R^4$, $R^5$, $R^7$, $X^1$ and $X^2$ are the same as defined above, can also be prepared by (D) reducing a compound of the formula:

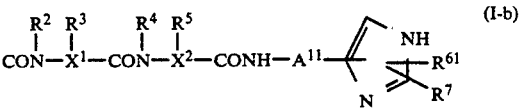 (I-b)

wherein $A^{11}$ is a lower alkoxycarbonyl-substituted lower alkylene group and $R^1$, $R^2$, $R^3$, $R^4$, $R^5$, $R^{61}$, $R^7$, $X^1$ and $X^2$ are the same as defined above, or a salt thereof.

Further, a compound of the formula:

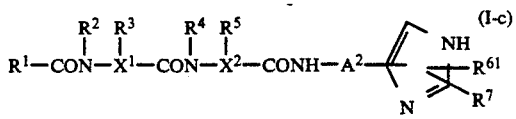 (I-c)

wherein $A^2$ is alkylene group substituted with a group of the formula:

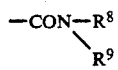

(wherein the symbols are the same as defined above) can be prepared by (E) reacting the compound (I-b) or a salt thereof with an amine compound of the formula:

 (VIII)

wherein the symbols are the same as defined above, or a salt thereof.

In the above-mentioned reactions, the compounds (III), (V), (VII), (VIII) and (I-b) may be used either in free form or in the form of a salt thereof. It is preferred to use the salts of these compound in the form of an acid addition salt. Examples of the salt include inogranic acid addition salts such as hydrochloride, hydrobromide, sulfate or nitrate, organic acid addition salts such as p-toluenesulfonate, methansulfonate or trifluoroacetate, and so forth. Further, the compounds (II), (IV) and (VI) may be in the form of a salt thereof, and examples of the salt include an alkali metal salt, a trialkylamine salt or pyridine salt.

Suitable examples of the reactive derivative of the compounds (II), (IV), and (VI) include the corresponding acid halides (e.g., acid chloride, acid bromide), mixed anhydrides (e.g., a mixed anhydride with alkyl carbonate), active esters (e.g., ester with pentachlorophenol, p-nitrophenol, 2,4-dinitrophenol, N-hydroxysuccinimide, N-hydroxyphthalimide, 1-hydroxybenzotriazole or 1-hydroxy-2-pyrrolidone), acid azide and other reactive derivatives such as amide with imidazole, 4-substituted-imidazole or triazole.

Methods of (A), (B) and (C)

The condensation of the compound (II) or a reactive derivative thereof with the compound (III) or a salt thereof, the condensation of the compound (IV) or a reactive derivative thereof with the compound (V) or a salt thereof and the condensation of the compound (VI) or a reactive derivative thereof with the compound (VII) or a salt thereof can be accomplished in conventional manners for the synthesis of peptides. For example, when the compound (II), (IV) or (VI) is employed in the form of the reactive derivative thereof, the condensation reaction can be conducted either in the presence or absence of an acid acceptor in a solvent. Suitable examples of the acid acceptor include alkali metal hydroxides (e.g., sodium hydroxide, potassium hydroxide), alkali metal carbonates (e.g., sodium carbonate, potassium carbonate), alkali metal bicarbonates (e.g., sodium bicarbonate, potassium bicarbonate), trialkylamines (e.g., trimethylamine, triethylamine), N,N-dialkylanilines (e.g., N,N-dimethylaniline, N,N-diethylaniline), pyridine, N-alkylmorpholines (e.g., N-methylmorpholine), and so forth. Dioxane, tetrahydrofuran, acetonitrile, chloroform, methylene chloride, dimethylformamide, N,N-dimethylacetamide, ethyl acetate, pyridine, acetone and water are suitable as the solvent.

On the other hand, when the compound (II), (IV) or (VI) is employed in the form of the free acid or a salt thereof, the condensation reaction can be conducted in the presence of a dehydrating agent in a solvent. Suitable examples of the dehydrating agent include N,N'-dicyclohexycarbodiimide, N-cyclohexyl-N'-morpholinocarbodiimide, N-ethyl-N'-(3-dimethylaminopropyl) carbodiimide, phosphorus oxychloride, phosphorus trichloride, thionyl chloride, oxalyl chloride, triphenylphosphine and the like. Vilsmeir reagents prepared from dimethylformamide and phosphorus oxychloride, from dimethylformamide and oxalyl chloride, from dimethylformamide and phosgen or from dimethylformamide and thionyl chloride may also be used as said dehydrating agent. The same solvent as mentioned in the condensation of the reactive derivative may be used in this step.

Method (D)

The reduction reaction of the compound (I-b) or a salt thereof can be accomplished by treating it with a reducing agent in a solvent. Examples of the reducing agent include sodium borohydride, calcium borohydride or lithium borohydride. Tetrahydrofuran, isopropanol, ethanol and methanol can be used as the solvent.

Method (E)

The reaction of the compound (I b) or a salt thereof with the compound (VIII) can be accomplished in a solvent. Methanol, ethanol, dimethylformamide and the like are suitable as the solvent.

It is preferred to carry out the above-mentioned reactions (A) to (E) at a temperature of $-50°$ to $50°$ C.

The desired compound (I), the starting compounds (II) to (V) and (VII) include either optical isomers due to the asymmetric carbon atom(s) or a mixture thereof. Since the above-mentioned reactions of the invention proceed without racemization, the compound (I) is readily obtained in the form of an optically active isomer by the use of the corresponding optically active isomers of the starting compounds.

As mentioned hereinbefore, the compound (I) of the invention or a salt thereof shows a potent immunomodulatory effect. Especially, the compound (I) activates the migration of macrophage (i.e., the macrophage staying in a chronic inflammatory part) to allow it to leave the inflammatory part, and, at the same time, the compound (I) inhibits delayed type hypersensitivity. Therefore, the compound (I) is useful for the treatment and/or prophylaxis of autoimmune diseases such as rheumatoid arthritis, multiple sclerosis, systemic lupus erythematodes, glomerulonepherits, rheumatic fever or type I diabetes and atopic allergy.

The imidazole-containing peptide (I) of the invention can be used for pharmaceutical use either in the form of a free base or a salt. Pharmaceutically acceptable salts of the compound (I) include, for example, inorganic acid addition salts such as hydrochloride, hydrobromide, phosphate and sulfate, and organic acid addition salts such as oxalate, acetate, lactate, citrate, tartrate, fumalate, maleate, aspartate, methanesulfonate and benzoate.

The imidazole-containing peptide (I) or a salt thereof may be administered either orally or parenterally to a warm-blooded animal, including human beings, and may also be used in the form of a pharmaceutical preparation containing the same compound in admixture with pharmaceutical excipients suitable for oral or parenteral administration. The pharmaceutical preparations may be in solid form such as tablets, granules, capsules and powders, or in liquid form such as solutions, suspensions or emulsions. Moreover, when administered parenterally, it may be used in the form of injections.

The dose of the imidazole-containing peptide (I) or a salt thereof may vary depending on the route of administration, the age, weight and condition of the patient and a kind of disease, and is preferably about 0.01 to 100 mg/kg a day, especially 0.1 to 30 mg/kg a day.

The starting compounds (III), (V) and (VIII) can be prepared in conventional manners for the peptide synthesis. For example, the starting compound (III) can be prepared by condensing a compound of the formula:

wherein $Y^1$ is an amino-protecting group, and $R^4$, $R^5$ and $X^2$ are the same as defined above, or a reactive derivative thereof with the compound (V) or a salt thereof, and removing the protecting group from the product. The compound (IV) can be prepared by condensing the compound (II) or a reactive derivative with a compound of the formula:

wherein $Y^2$ is a carboxy-protecting group, and $R^4$, $R^5$ and $X^2$ are the same as defined above, or a salt thereof, and removing the protecting group from the product. Further, the compound (VII) can be prepared by condensing a compound of the formula:

wherein the symbols are the same as defined above, or a reactive derivative thereof with the compound (III) or a salt thereof, or condensing a compound of the formula:

wherein the symbols are the same as defined above, or a reactive derivative thereof with the compound (V) or a salt thereof, and removing the protecting group from the product.

In the above-mentioned reactions, a wide variety of protecting groups which have been usually employed to protect amino or carboxy group(s) in the peptide synthesis can be used as the protecting group or groups ($Y^1$ and/or $Y^2$).

EXPERIMENT 1

Effect on alveolar macrophage migration

Method

Japanese white female rabbits, weighing between 3 and 4 kg, were sacrificed under anesthesia. Alveolar macrophages were obtained by pulmonary lavage with saline.

In a "test group", the macrophages were migrated in the RPMI-1640 medium containing 5% rabbit serum and $10^{-7}$M of a test compound. Said migration test was carried out at 37° C. for 24 hours according to the method described in Journal of Leukocyte Biology 42: 197–203 (1987). The resulting migration was projected at about 15 times magnification and traced. Then, the migration area was measured with a planimeter.

The migration test in a "positive control group" was carried out by the use of the RPMI-1640 medium containing 5% rabbit serum and 5 mM of L-fucose; instead of the medium containing the test compound. On the other hand, the experiment in a "control group" was carried out by the use of a medium containing 5% rabbit serum only. The migration index was calculated by the following formula:

$$\text{Migration index} = \frac{\left(\begin{array}{c}\text{migration area of}\\\text{test group}\end{array}\right) - \left(\begin{array}{c}\text{migration area}\\\text{of control group}\end{array}\right)}{\left(\begin{array}{c}\text{migration area of}\\\text{positive control}\\\text{group}\end{array}\right) - \left(\begin{array}{c}\text{migration area}\\\text{of control group}\end{array}\right)} \times 100$$

Results

The migration index of all of compounds shown in Table 1 were more than 100.

TABLE 1

| Ex. | Test Compounds |
|---|---|
| 1 | BOC—L—Phe—L—Phe—L—His—OMe |
| 5 | 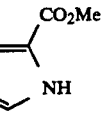 |
| 6 | 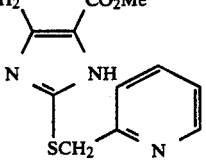 |

TABLE 1-continued

| | |
|---|---|
| 7 | 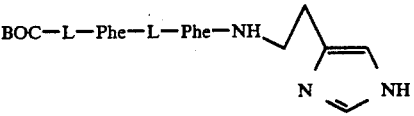 |
| 9 | 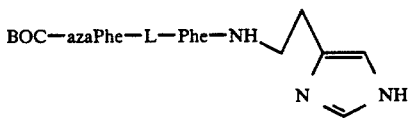 |
| 10 | t-BuCO—L—Phe—L—Phe—L—His—OMe |
| 11 | BOC—L—Phe—L—Phe—L—His—NH$_2$ |
| 13 | BOC—azaPhe—L—Phe—L—His—OMe |
| 14 | 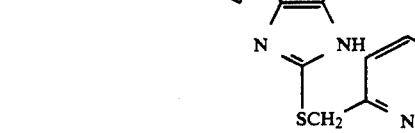 |
| 15 | 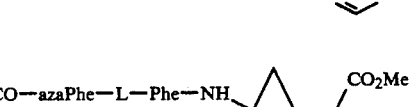 |
| 17 | 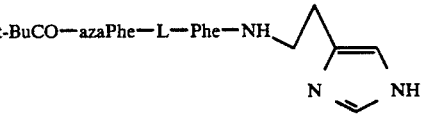 |
| 18 | 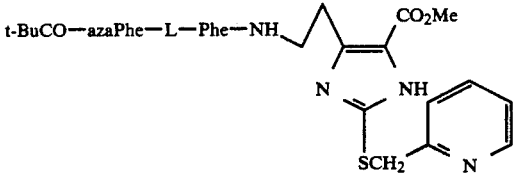 |
| 19 | 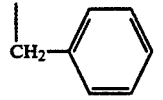 |

Note: In Table 1, the meanings of the abbreviations are as follows:

| Abbreviations | Meanings |
|---|---|
| BOC | tert.-butyloxycarbonyl |
| Me | methyl |
| t-Bu | tert.-butyl |
| His | histidine |
| Phe | phenylalanine |
| azaPhe | 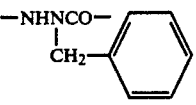 |

EXPERIMENT 2

Inhibitory effect on picryl chloride-induced delayed type hypersensitivity

Method

BALB/C female mice (10-week-old) were sensitized by spreading one ml of an ethanol solution containing 7 w/v % of picryl chloride to abdominal skin of the mice. In a "test group", a test compound was administered orally to the mice a day for 7 days from the day of sensitization.

7 Days after the sensitization, 10 μl of an olive oil solution containing 1 w/v % of picryl chloride was spread to both side skin of left external ear. 24 Hours later, the mice was sacrificed and the thickness of both ears was immediately measured.

The inhibition (%) of swelling of exterernal ear was calculated according to the following formula:

$$\left[1 - \frac{\begin{pmatrix}\text{thickness of left}\\\text{external ear of}\\\text{test group}\end{pmatrix} - \begin{pmatrix}\text{thickness of right}\\\text{external ear of}\\\text{test group}\end{pmatrix}}{\begin{pmatrix}\text{thickness of left}\\\text{external ear of}\\\text{control group}\end{pmatrix} - \begin{pmatrix}\text{thickness of right}\\\text{external ear of}\\\text{control group}\end{pmatrix}}\right] \times 100$$

Results

The results are shown in the following Table 2.

TABLE 2

| Test Compounds | Dose (mg/kg) | Inhibition (%) of swelling of external ear |
|---|---|---|
| BOC—azaPhe—L—Phe—L—His—OMe | 10 | 72.6 |
| BOC—azaPhe—L—Phe—NH—[imidazole] | 2 | 70.1 |
| t-BuCO—azaPhe—L—Phe—NH—[imidazole] | 2 | 68.5 |
| BOC—azaPhe—L—Phe—NH—[CO₂Me, SCH₂-pyridine] | 10 | 65.1 |
| t-BuCO—azaPhe—L—Phe—NH—[CO₂Me, SCH₂-pyridine] | 10 | 55.0 |
| Control | — | 0 |

Note: In Table 2, the abbreviations are the same as defined in Table 1.

EXAMPLE 1

L-Phenylalanyl-L-histidine methyl ester dihydrobromide(1.75 g) is dissolved in a mixture of dimethylformamide (10 ml) and triethylamine(1.4 ml), and N-tert-butoxycarbonyl-L-phenylalanine succinimido ester (1.34 g) is added thereto. The mixture is stirred at room temperature overnight. Ethyl acetate is added to the mixture, and insoluble materials are filtered off. The filtrate is washed with an aqueous sodium bicarbonate solution, and an aqueous sodium chloride solution is added thereto. The precipitated crystals are washed with ethyl acetate and water and then dried to give N-tert-butoxycarbonyl-L-phenylalanyl-L-phenylalanyl-L-histidine methyl ester(1.5 g) as colorless crystals. Yield: 71.8%

M.p. 170°–173° C. (dec.) Nujol

IR ν (cm$^{-1}$) :3310, 3300, 1740, 1695, 1640 Max

NMR (d$_6$-DMSO) δ: 1.28(9H,s), 2.4–3.2(6H,m), 3.59(3H,s), 3.9–4.8(3H,m), 6.65–7.6(14H,m), 7.8–8.2(1H,m), 8.37–8.7(1H,m)

EXAMPLE 2

N-tert-Butoxycarbonyl-L-2-amino-4-phenylbutyric acid dicyclohexylamine salt (1.84 g) is dissolved in a mixture of ethyl acetate and an aqueous 3% potassium bisulfate solution, and the ethyl acetate layer is separated, washed with water, dried and then concentrated to remove solvent. The residue is dissolved in dimethyformamide (20 ml) and L-phenylalanyl-L-histidine methyl ester dihydrobromide (1.91 g), N-hydroxysuccinimide(0.5 g) and dicyclohexylcarbodiimide (0.9 g) are added thereto. Triethylamine (1.4 ml) is added to the mixture under cooling, and the mixture is stirred at room temperature overnight. After the reaction, ethyl acetate is added to the mixture, and insoluble materials are filtered off and then the filtrate is concentrated under reduced pressure to remove solvent. The residue is purified by silica gel column chromatography (solvent: chloroform:methanole=9:1) and crystallized with ethyl acetate to give N-tert-butoxycarbonyl-L-2-amino-4-phenyl butyryl-L-phenylalanyl-L-histidine methyl ester (1.45 g). Yield; 61%

M.p. 186°-187° C. (dec.) Nujol

IR $\nu$ (cm$^{-1}$) :3300, 1730, 1685, 1660, 1645 Max

NMR (d6 DMSO) δ: 1.36(9H,s), 1.5-1.9(2H,m), 2.35-3.5(6H,m), 3.53(3H,s), 3.7-4.0(1H,m), 4.3-4.7(2H,m), 6.7-7.45(14H,m), 7.8-8.1(1H,m), 8.4-8.7(1H,m)

EXAMPLE 3

(1) N-tert-Butoxycarbonyl-L-2-amino-4-phenylbutyric acid (2.79 g), L-histidine methyl ester dihydrochloride (2.42 g), 1-hydroxybenzotriazole (1.35 g) and triethylamine (2.8 ml) are dissolved in dimethylformamide (20 ml), and dicyclohexylcarbodiimide (2.1 g) is added thereto under ice-cooling. The mixture is stirred at room temperature overnight. Ethyl acetate is added to the reaction mixture, and insoluble materials are filtered off. The filtrate is washed with an aqueous sodium bicarbonate solution and an aqueous sodium chloride solution, dried, and then concentrated to remove solvent. The residue is crystallized with ether to give N-[N-tert-butyoxycarbonyl-L-2-amino-4-phenylbutyryl]-L-histidine methyl ester (3.3 g) as white crystals. Yield ; 76.6%

M.p. 127°-130° C. Nujol

IR $\nu$ (cm$^{-1}$) :3320, 1740, 1685, 1650 Max

NMR (CDCL$_3$) δ: 1.42(9H,s), 1.7-2.4(2H,m), 2.68(2H,t), 3.12(2H,d), 3.66(3H,s), 3.95-4.3(1H,m), 4.65-5.0(1H,m), 6.3-6.65(1H,m), 6.75(1H,s), 7.0-7.4(5H,m), 7.48(1H,s), 7.4-7.8(1H,m)

(2) The product (2.15 g) obtained in Paragraph (1) is dissolved in 20% hydrogenbromide - acetic acid solution (20 ml) and the mixture is stirred at room temperature for an hour. The reaction mixture is concentrated under reduced pressure to remove solvent and the residue is triturated with ether to give N-(L-2-amino-4-phenylbutyryl)-L-histidine methyl ester dihydrobromide. The product is dissolved in dimethylformamide (20 ml), and N-tert-butoxycarbonyl-L-phenylalanine succinimido ester (1.81 g) and triethylamine (2.1 ml) are added thereto.

The mixture is stirred overnight. The reaction mixture is treated in the same manner as described in Example 2 and crystallized with ether to give N-(N tert-butoxycarbonyl L-phenylalanyl)-L-2-amino-4-phenylbutyryl-L-histidine methyl ester (3.3 g) as white crystals. Yield ; 69.2%

M.p. 186-189° C. Nujol

IR $\nu$ (cm$^{-1}$) :3300, 1740, 1695, 1640 Max

NMR (CDCl$_3$+d$_6$-DMSO) δ: 1.35(9H,s), 1.7-2.3(2H,m), 2.5-3.2(6H,m), 3.64(3H,s), 4.2-4.8(3H,s), 6.2-6.5(1H,m), 6.78(1H,s), 7.0-7.4(10H,m), 7.46(1H,s), 7.8-8.3(2H,m)

EXAMPLE 4

(1) N-Benzyloxycarbonyl-L-phenylalanine (2.99 g) and p-nitrophenol (1.39 g) are dissolved in tetrahydrofuran (30 ml), and dicyclohexylcarbodiimide (2.1 g) is added thereto under ice-cooling. The mixture is stirred at room temperature for four hours and insoluble materials are filtered off. Ethyl acetate is added to the filtrate and the mixture is washed with an aqueous sodium bicarbonate solution and an aqueous sodium chloride solution, dried, and then concentrated to remove solvent. Hexane is added to the residue to give N-benzyloxycarbonyl-L-phenylalanine-p-nitrophenyl ester as crystals. The product is dissolved in tetrahydrofuran (20 ml), and a solution(15 ml) of L-histidine methyl ester dihydrochloride (2.4 g) and triethylamine (2.8 ml) in water is added thereto under ice-cooling, and the mixture is stirred at room temperature overnight. The reaction mixture is concentrated under reduced pressure to remove solvent. The residue is purified by silica gel column chromatography (solvent; chloroform:methanol = 15:1) and crystallized with ethyl acetate to give N-benzyloxycarbonyl-L-phenylalanyl-L-histidine methyl ester (2.8 g) as colorless crystals. Yield ; 64.1%

M.p. 113-116° C. Nujol

IR $\nu$ (cm$^{-1}$) :3280, 1745, 1710, 1655 Max

NMR (d$_6$-DMSO) δ: 2.6-3.2(4H,m), 3.59(3H,s), 4.1-4.7(2H,m), 4.95(2H,s), 6.8-7.6(9H,m), 8.35-8.6(1H,m)

(2) The product (2.49 g) obtained in Paragraph (1) is dissolved in 25% hydrogenbromide acetic acid solution (30 ml) and the solution is stirred at room temperature for an hour. The reaction mixture is concentrated under reduced pressure and the residue is triturated with ether to give L-phenylalanyl-L-histidine methyl ester dihydrobromide as a crude product. A mixture of the product (1.75 g) thus obtained, N-benzyloxycarbonyl-L-phenylalanine p-nitrophenyl ester(1.55 g), triethylamine (1.4 ml) and dimethylformamide (10 ml) is stirred at room temperature overnight. The reaction mixture is concentrated under reduced pressure, and ethyl acetate and water are added to the residue. The precipitated crystals are collected by filtration to give N-benzyloxycarbonyl-L-phenylalanyl-L-phenylalanyl-L-histidine methyl ester (1.02 g). Yield ; 46.2%

M.p. 204-206° C. Nujol

IR $\nu$ (cm$^{-1}$) :3310, 3290, 1740, 1695, 1640 Max

NMR (d$_6$-DMSO) δ: 2.4-3.2(6H,m), 3.58(3H,s), 4.0-4.75(3H,m), 4.92(2H,s), 6.7-7.6(19H,m), 7.9-8.25(1H,m), 8.25-8.6(1H,m)

EXAMPLE 5

4-[2-(N-Benzyloxycarbonylamino)ethyl]5-methoxycarbonylimidazole (1.2 g) is dissolved in 30% hydrogenbromide acetic acid solution (20 ml) and the solution is stirred at room temperature for 30 minutes. The reaction mixture is concentrated under reduced pressure and the residue is triturated with ether to give 4-(2-aminoethyl)-5-methoxycarbonylimidazole dihydrobromide. To the thus-obtained product are added dimethylformamide (20 ml), N-tert-butoxycarbonyl-L-phenylalanyl-L-phenylalanine (1.65 g) and 1-hydroxybenzotriazole (0.54 g). Dicyclohexylcarbodiimide (0.83 g) is added to the mixture under ice-cooling and the mixture is stirred for 10 minutes. Triethylamine (1.4 ml) is added to the mixture and the mixture is stirred at room temperature overnight. Ethyl acetate is added to the reaction mixture, and insoluble materials are filtered off. The filtrate is washed with an aqueous sodium bicarbonate solution and an aqueous sodium chloride solution, dried, and then concentrated to remove solvent. The residue is purified by silica gel column chromatography (solvent; chloroform:methanol = 12:1) and crystallized with ether to give 4-{2-[N-(N-tert-butoxycarbonyl-L-phenylalanyl-L-phenylalanyl) amino]ethyl}-5-methoxycarbonylimidazole (1.4 g) as colorless crystals. Yield ; 62.2%

M.p. 155-159° C. KBr

IR ν (cm$^{-1}$) :3370, 3280, 1710, 1690, 1650 Max

NMR (CDCl$_3$+d$_6$-DMSO) δ: 1.33(9H,s), 2.9-3.7(8H,m), 3.82(3H,s), 4.2-4.8(2H,m), 5.48(1H,brs), 6.9-7.5(11H,m), 7.50(1H,s)

EXAMPLES 6 to 8

N-tert-butoxycarbonyl-L-phenylalanyl-L-phenyl alanine [or N-benzyloxycarbonyl-L-phenylalanyl-L-phenylalanine] and 4-aminomethyl-5-methoxycarbonyl-2 -(2-pyridylmethylthio) imidazole [or 4-(2-aminoethyl)-5-methoxycarbonyl-2-(2-pyridylmethylthio)imidazole] are treated in the same manner as described in Example 5 to give the following compounds.

(6) 4 [N (N-tert-butoxycarbonyl-L-phenylalanyl-L-phenylalanyl)aminomethyl]-5-methoxycarbonyl-2-(2-pyridylmethylthio)imidazole M.p. 147-150° C. KBr IR ν (cm$^{-1}$) :3280, 1705, 1690, 1645 Max NMR (d$_6$-DMSO) δ: 1.26(9H,s), 2.5-3.1(4H,m), 3.70(3H,s), 3.9-4.7(6H,m), 6.6-8.5(17H,m), 12.3-13.0(1H,br)

(7) 4-{2 [N (N-tert-butoxycarbonyl-L-phenylalanyl-L-phenylalanyl)amino]ethyl}-5-methoxycarbonyl-2-(2-pyridylmethylthio)imidazole M.p. 182-184° C. (dec.) Nujol IR ν (cm$^{-1}$) :3275, 1705, 1690, 1645 Max NMR (d$_6$-DMSO) δ: 1.26(9H,s), 2.4-3.1(4H,m), 3.1-3.3(2H,m), 3.68(3H,s), 3.8-4.6(6H,m), 6.7-8.4(17H,m)

(8) 4 [N-(N-benzyloxycarbonyl-L-phenylalanyl-L-phenylalanyl)aminomethyl]-5-methoxycarbonyl-2-(2-pyridylmethylthio)imidazole M.p. 140°-142° C. Nujol IR ν (cm .1) :3270, 1720, 1695, 1640 Max NMR (d$_6$-DMSO) δ:2.6-3.2(4H,m), 3.70(3H,s), 4.0-4.7(6H,m), 4.84(2H,s), 6.8-8.45(22H,m), 12.5-13.0(1H,br)

EXAMPLE 9

Triethylamine (3.5 ml) is added to a mixture of histamine dihydrochloride (1.84 g), N-tert-butoxycarbonyl-L-phenylalanine succinimido ester (3.62 g), dimethylformamide (20 ml) and water (5 ml) under ice-cooling and then the mixture is stirred at room temperature for three hours. The reaction mixture is concentrated under reduced pressure to remove solvent and ethyl acetate is added to the residue and then, insoluble materials are filtered off. The filtrate is washed with an aqueous sodium bicarbonate solution and water, dried, and then concentrated to remove solvent. The residue is crystallized with ether to give N-(N-tert-butoxycarbonyl-L-phenylalanyl)histamine (2.5 g). The product (1.79 g) thus obtained is dissolved in 15% hydrogenbromideacetic acid solution and the solution is stirred at room temperature for 30 minutes. The reaction mixture is concentrated under reduced pressure to give N-(L-phenylalanyl) histamine dihydrobromide (2.1 g). The thus-obtained product (2.1 g) is dissolved in dimethylformamide, and N-tert-butoxycarbonyl-L-phenylalanine succinimido ester (1.81 g) and triethylamine (2.1 ml) are added thereto and then the mixture is stirred overnight. Ethyl acetate is added to the reaction mixture, and insoluble materials are filtered off. The filtrate is washed with an aqueous sodium bicarbonate solution and an aqueous sodium chloride solution and dried, and then concentrated to remove solvent. The residue is purified by silica gel column chromatography (solvent; chloroform:methanol=9:1) and crystallized with ether to give N-(N-tert-butoxycarbonyl-L-phenylalanyl L-phenylalanyl)histamine (1.88 g) as white crystals. Yield ; 74.3%

M.p. 175-177° C. KBr

IR ν (cm$^{-1}$) :3300, 1690, 1650 Max

NMR (CDCl$_3$+d$_6$-DMSO) δ: 1.33(9H,s), 2.5-3.6(6H,m), 4.2-5.5(5H,m), 6.71(1H,s), 6.9-7.4(12H,m), 7.48(1H,s)

EXAMPLE 10

10% Hydrogenchloride dioxane solution (30 ml) is added to N-tert-butoxycarbonyl-L-phenylalanyl-L-phenylalanyl-L-histidine methyl ester (2.25 g) and the mixture is stirred at room temperature for two hours. The reaction mixture is concentrated under reduced pressure to remove solvent and ether is added to the residue to give L phenylalanyl-L phenylalanyl-L-histidine methyl ester dihydrochloride (2.15 g) as white powder. The product (2.15 g) thus obtained is dissolved in dimethylformamide (15 ml), and pivaloyl chloride (0.48 g) is added thereto. Triethylamine (2.24 ml) is added dropwise to the mixture under ice-cooling and the mixture is stirred at room temperature overnight. Ethyl acetate is added to the reaction mixture and insoluble materials are filtered off. The filtrate is washed with an aqueous sodium bicarbonate solution and water, dried, and then concentrated to remove solvent. The residue is purified by silica gel column chromatography (solvent; chroroform:methanol=12:1) and triturated with ether to give N-pivaloyl-L-phenylalanyl-L-phenylalanyl-L-histidine methyl ester (0.98 g). Yield ;44.8%

M.p. 128-131° C. KBr

IR ν (cm .1) :3380, 3280, 1740, 1645 Max

NMR (d$_6$-DMSO) δ: 0.96(9H,s), 2.6-3.3(6H,m), 3.59(3H,s), 4.3-4.8(3H,m), 6.83(1H,s), 7.0-7.5(12H,m), 7.53(1H,s), 7.49(1H,d), 7.94(1H,d)

EXAMPLE 11

N-tert-butoxycarbonyl-L-phenylalanyl-L-phenylalanyl-L-histidine methyl ester (2 g) is dissolved in a methanol solution saturated with ammonia, and the solution is stirred in a pressure bottle at room temperature for three days. The reaction mixture is concentrated under reduced pressure and the residue is crystallized with ether to give N-tert-butoxycarbonyl-L-phenylalanyl-L-phenylalanyl-L-histidine amide (1.7 g) as white crystals. Yield: 87.2%

M.p. 169.6°-171° C. (decomp.) KBr

IR ν (cm$^{-1}$) :3380, 3300, 1670 Max

NMR (d$_6$-DMSO) δ: 1.26(9H,s), 2.4-3.2(6H,m), 3.9-4.8(3H,m), 6.65-7.6(13H,m), 7.9-8.3(2H,m)

EXAMPLE 12

N-Pivaloyl-L-phenylalanyl-L phenylalanyl-L-histidine methyl ester (1.90 g) is dissolved in tetrahydrofuran (12 ml), and a solution of sodium borohydride (0.20 g) in methanol (2.5 ml) is added dropwise thereto. The mixture is stirred at room temperature for four hours, and 5% hydrochloric acid (4 ml) is added to the mixture and then the solvent is distilled off. The residue is made alkaline with an aqueous sodium bicarbonate solution and then extracted with ethyl acetate. The extract is washed with an aqueous sodium chloride solution, dried, and concentrated to remove solvent. The residue is triturated with ethyl acetate to give 4-{2-hydroxymethyl-2-[N-(N-pivaloyl-L-phenylalanyl-L-phenylalanyl)amino]ethyl}imidazole (1.24 g) as white powder. Yield: 68.8%

M.p. 124–130° C. Nujol

IR ν (cm⁻¹) :3300, 1640 Max

NMR (d₆-DMSO) δ: 0.97(9H,s), 2.3-3.5(6H,m), 3.7-4.1(2H,m), 4.3-4.7(3H,m), 6.6-8.3(16H,m)

MS (m/z): 519 (M+)

EXAMPLE 13

(1) A solution of phosgene (2.6 g) in dichloromethane (25 ml) is added dropwise to a mixture of L-phenylalanine methyl ester hydrochloride (4.3 g), triethylamine (6.4 ml) and dichloromethane (25 ml) at a temperature below −30° C. The mixture is stirred at 30° C. for 30 minutes and concentrated under reduced pressure to remove solvent. Dimethylformamide (30 ml), N-tert-butoxycarbonyl-N'-benzylhydrazine (4.44 g) and triethylamine (3.64 ml) are added to the residue and the mixture is stirred at 50° C. for five hours and further stirred at room temperature overnight. The reaction mixture is concentrated under reduced pressure to remove solvent, and ethyl acetate and water are added to the residue. Organic layer is collected, washed with water, dried and then concentrated to remove solvent. The residue is purified by silica gel column chromatography (solvent; toluene:ethyl acetate=8:1) and triturated with hexane to give 3-tert-butoxycarbonyl-2-benzylcarbazoyl-L-phenylalanine methyl ester (4 g) as white powder. Yield ;93.5%

M.p. 71–73° C. KBr

IR ν (cm .1) :3400, 3240, 1730, 1650 Max

NMR (CDCL₃) δ: 1.42(9H,s), 3.13(2H,d), 3.69(3H,s), 4.4-5.1(3H,m), 5.89(1H,brd), 6.01(1H,s), 7.0-7.5(10H,m)

(2) The product (1.71 g) obtained in Paragraph (1) is dissolved in methanol (5 ml). An aqueous 2N-sodium hydroxide solution (2.2 ml) is added to the solvent and the mixture is stirred at room temperature for three hours. After the reaction, methanol is distilled off under reduced pressure and the residue is acidified with 10% citric acid and then the mixture is extracted with ethyl acetate. The extract is washed with an aqueous sodium chloride solution, dried and then concentrated to remove solvent, whereby 3 tert-butoxycarbonyl-2-benzylcarbazoyl-L-phenylalanine (1.65 g) is obtained as crude crystals. The thus-obtained product (1.65 g) is dissolved in dimethylformamide (20 ml), and L-histidine methyl ester dihydrochloride (1.07 g), triethylamine (1.26 ml), 1-hydroxybenzotriazole (0.54 g) and dicyclohexylcarbodiimide (0.91 g) are added thereto under ice-cooling. The mixturte is stirred at room temperature overnight. Ethyl acetate is added to the reaction mixture, and insoluble materials are filtered off. The filtrate is washed with an aqueous sodium bicarbonate solution and water ,dried and then concentrated to remove solvent. The residue is purified by silica gel column chromatography (solvent; chloroform:methanol=12:1) and triturated with ether to give 3-tert-butoxycarbonyl-2-benzylcarbazoyl-L-phenylalanyl-L-histidine methyl ester (1.76 g) as colorless powder. Yield ; 77.9% Nujol IR ν (cm⁻¹) :3400, 3270, 1730, 1655 Max NMR (CDCL₃) δ: 1.40(9H,s), 2.9-3.3(4H,m), 3.65(3H,s), 4.4-5.0(4H,m), 6.07(1H,d), 6.65-6.9(1H,m), 6.70(1H,s), 7.0-7.5(1H,m), 7.39(1H,m)

EXAMPLES 14 to 15

3-tert-Butoxycarbonyl-2-benzylcarbazoyl-L-phenylalanine and histamine dihydrochloride or 4-(2-aminoethyl)-5-methoxycarbonyl-2-(2-pyridylmethylthio)imidazole trihydrobromide are treated in the same manner as described in Example 13 (2) to give the following compounds.

(14) N-(3-tert-Butoxycarbonyl-2-benzylcarbazoyl-L-phenylalanyl)histamine KBr

IR ν (cm⁻¹) :3480, 3250, 1715, 1645 Max

NMR (CDCL₃) δ: 1.35(9H,s), 2.5-2.8(2H,m), 2.9-3.5(4H,m), 4.3-4.8(3H,m), 6.03(1H,brd), 6.63(1H,s), 6.9-7.4(12H,m)

(15) 4-[2-((3-tert-Butoxycarbonyl-2-benzylcarbazoyl-L-phenylalanyl)amino)ethyl]5-methoxycarbonyl-2-(2-pyridylmethylthio)imidazole M.p. 132–137° C. Nujol IR ν (cm⁻¹) :3250, 1710, 1660 Max NMR (CDCL₃) δ: 1.38(9H,s),-2.9-3.8(8H,m), 3.82(2H,s), 4.0-4.9(3H,m), 5.9-6.2(1H,m), 6.9-8.0(15H,m) Examples 16 to 18

L-Phenylalanine methyl ester and N-tert-butoxycarbonyl-N'-phenethylhydrazine or N pivaloyl-N'-benzylhydrazine hydrobromide are treated in the same manner as described in Example 13-(1) to give the following compounds.

3-tert-Butoxycarbonyl-2-phenethylcarbazoyl-L-phenylalanine methyl ester

M.p. 97–99° C. Nujol

IR ν (cm⁻¹) :3400, 3190, 1735, 1640 Max

NMR (CDCL₃) δ: 1.41(9H,s), 2.73-3.2(4H,m), 3.65(3H,s), 3.4-4.0(2H,m), 4.6-4.9(1H,m), 5.71(1H,d), 5.96(1H,S), 6.96-7.42(10H,m)

3-Pivaloyl-2-benzylcarbazoyl-L-phenylalanine methyl ester

M.p. 141–143° C. Nujol

IR ν (cm⁻¹) :3290, 1725, 1665, 1645 Max

NMR (CDCL₃) δ: 1.03(9H,s), 3.13(2H,d), 3.70(3H,s), 4.40-5.10(4H,m), 5.50-5.70(1H,m), 6.9-7.50(10H,m)

The compounds obtained above and histamine dihydrochloride or 4-(2-aminoethyl)-5-methoxycarbonyl-2-(2-pyridylmethylthio)imidazole trihydrobromide are treated in the same manner as described in Example 13-(2) to give the following compounds.

(16) N-(3-tert-butoxycarbonyl-2-phenethylcarbazoyl-L-phenylalanyl)histamine

M.p. 87–95° C. Nujol

IR ν (cm⁻¹) :3290, 1715, 1645 Max

NMR (CDCL₃) δ: 1.39(9H,s),-2.56-4.0(2H,d), 4.3-4.6(4H,m), 5.88(1H,d), 6.66(1H,S), 7.0-7.4(1H,m), 7.42(1H,s), 8.1-8.4(1H,m)

(17) N-(3-Pivaloyl-2-benzylcarbazoyl-L-phenylalanyl)histamine

M.p. 78 86° C. KBr

IR ν (cm⁻¹) :3400, 3300, 1650 Max

NMR (CDCL₃) δ: 0.98(9H,s), 2.6-3.6(2H,d), 4.4-5.0(3H,m), 5.55(1H,d), 6.61(1H,S), 6.95-7.5(10H,m), 8.2-8.9(2H,m)

(18) 5-Methoxycarbonyl-4-[2-((3-pivaloyl-2-benzylcarbazoyl-L-phenylalanyl)amino)ethyl] -2-(2-pyridylmethylthio)imidazole M.p. 171–172° C. KBr IR ν (cm⁻¹) :3400, 1705, 1660 Max NMR (CDCL₃) δ: 1.01(9H,s), 2.8–3.8(6H,m), 3.83(3H,s), 4.2–4.8(5H,m), 5.56–5.75(1H,m), 6.95–8.00(14H,m), 8.33–8.5(1H,m)

EXAMPLE 19

(1) To a mixture of N-(benzyloxycarbonyl)-L-2-aminoxy-3-phenylpropionic acid (3.09 g), L-histidine methyl ester dihydrochloride (2.42 g), N-hydroxy-benzotriazole (1.35 g), triethylamine (2.8 ml) and dimethylformamide(20 ml) is added dicyclohexylcarbodiimide (2.1 g) under ice-cooling, and the mixture is stirred at room temperature overnight. The reaction mixture is concentrated under reduced pressure to remove solvent, and ethyl acetate is added to the residue. Insoluble materials are filtered off. The filtrate is washed with an aqueous sodium bicarbonate solution and water, dried, and then concentrated to remove solvent. The residue is purified by silica gel column chromatography (solvent; chloroformethyl acetate=12:1) and crystallized with hexane to give N [N-(benzyloxycarbonyl)-L-2-aminoxy 3-phenylpropionyl] -L-histidine methyl ester(2.1 g) as white powder. KBr IR ν (cm⁻¹) 3300, 1735, 1665 Max NMR (CDCL₃) δ: 2.8–3.2(4H,m), 3.62(3H,s), 4.3–4.9(2H,m), 5.09(2H,s), 6.66(1H,s), 7.0–7.5(10H,m), 7.36(1H,s), 7.95(1H,d)

(2) The product (2.1 g) obtained in Paragraph (1) is dissolved in 33% hydrogenbromide acetic acid solution (30 ml) and the solution is stirred at room temperature for an hour. The reaction mixture is concentrated under reduced pressure to remove solvent and the residue is triturated with ether to give N-(L-2-aminoxy-3-phenylpropionyl)-L-histidine methyl ester dihydrobromide (2.32 g). The thus-obtained product (2.32 g) is suspended in dimethylformamide (20 ml), and N-tert-butoxycarbonyl-L-phenylalanine(1.25 g), 1-hydroxybenzotriazol(0.68 g) and triethylamine (1.3 ml) are added thereto. Dicycrohexylcarbodiimide (1.1 g) is added to the mixture under ice-cooling and the mixture is stirred at room temperature overnight. The reaction solution is concentrated under reduced pressure and ethyl acetate is added to the residue. Insoluble materials are filtered off. The filtrate is washed with an aqueous sodium bicarbonate solution and water, dried, and then concentrated to remove solvent. The residue is purified by silica gel column chromatography (solvent; chloroform :methanol=15:1) and triturated with isopropylether to give N-[N-(tert-butoxycarbonyl-L-phenylalanyl)-L-2-aminoxy-3-phenylpropionyl]-L-histidine methyl ester(1.95 g) as white powders. Yield ; 71.7% KBr IR ν (cm⁻¹) :3400, 3290, 1745, 1680 Max NMR (CDCL₃) δ: 1.35(9H,s), 2.7–3.4(6H,m), 3.70(3H,s), 4.0–5.0(3H,m), 5.0–5.5(1H,m), 6.74(1H,s), 7.0–8.3(11H,d)

EXAMPLE 20

To a mixture of N-(benzyloxycarbonyl)-L-2-aminoxy-3-phenylpropionic acid (1.6 g), L-phenylalanyl-L-histidine methyl ester dihydrobromide (2.39 g), N-hydroxysuccinimide(0.6 g), triethylamine (1.4 ml) and dimethylformamide(20 ml) is added dicyclohexyl carbodiimide (11 g) under ice-cooling and then the mixture is stirred at room temperature overnight. The reaction mixture is concentrated under reduced pressure to remove solvent and ethyl acetate is added to the residue. Insoluble materials are filtered off. The filtrate is washed with an aqueous sodium bicarbonate solution and water, dried, and then concentrated to remove solvent. The residue is purified by silica gel column chromatography (solvent; chloroform:methanol=9:1) and crystallized with ether to give N-[N-(benzyloxycarbonyl)-L-2-aminoxy-3-phenylpropionyl]-L-phenylalanyl-L-histidine methyl ester(1.3 g). KBr IR ν (cm⁻¹) :3300, 1735, 1650 Max NMR (CDCL₃) δ: 2.6–3.3(6H,m), 3.62(2H,s), 4.3–4.9(3H,m), 5.05(2H,s), 6.63(1H,s), 6.8–7.9(17H,m)

EXAMPLE 21

N-Pivaloyl-L-phenylalanine and N-methyl-L-phenylalanyl-L-histidine methyl ester are treated in the same manner as described in Example 1 to give N-pivaloyl-L-phenylalanyl-N-methyl-L-phenylalanyl-L-histidine methyl ester.

EXAMPLE 22

N-Pivaloyl-N-methyl-L-phenylalanine and L-N-methyl-phenylalanyl-L-histidine methyl ester are treated in the same manner as described in Example 1 to give N-pivaloyl-N-methyl-L-phenylalanine-L-phenylalanyl-L-histidine methyl ester.

EXAMPLE 23

N-(N-Pivaloyl-L-phenylalanyl)-N'-benzylhydrazine and L-histidine methyl ester are treated in the same manner as described in Example 13 to give N-pivaloyl-L-phenylalanyl-2-benzylcarbazoyl-L-histidine methyl ester.

EXAMPLE 24

N-(3-Pivaloyl-2-benzylcarbazoyl)-N'-benzylhydrazine and L-histidine methyl ester are treated in the same manner as described in Example 13 to give 3 (3-pivaloyl-2-benzylcarbazoyl)-2-benzylcarbazoyl-L-histidine methyl ester.

EXAMPLE 25

N-Pivaloyl-L-phenylalanine and L-2-aminoxy-3-phenylpropionyl-L-histidine methyl ester are treated in the same manner as described in Example 19 to give N-(N-pivaloyl-L-phenylalanyl)-L-2-aminoxy 3-phenylpropionyl-L-histidine methyl ester.

EXAMPLE 26

N-Pivaloyl-L-2-aminoxy-3-phenypropionic acid and L-2-aminoxy-3-phenylpropionyl-L-histidine methyl ester are treated in the same manner as described in Example 19 to give N-(N-pivaloyl-L-2-aminoxy-3-phenylpropionyl)-L-2-aminoxy-3-phenylpropionyl-L-histidine methyl ester.

EXAMPLES 27 to 32

The compounds obtained in Examples 21 to 26 are converted to their amides in the same manner as described in Example 11 to give the compounds shown in the following table 3.

TABLE 3

| No. | Compounds |
| --- | --- |
| 27 | t-BuCO—L—Phe—L—MePhe—L—His—NH₂ |
| 28 | t-BuCO—L—MePhe—L—MePhe—L—His—NH₂ |

TABLE 3-continued

| 29 | t-BuCO—L—Phe—NHN—CO—L—His—NH$_2$ (with CH$_2$Ph on N) |
| 30 | t-BuCO—NHN—CONHN—CO—L—His—NH$_2$ (with CH$_2$Ph on each N) |
| 31 | t-BuCO—L—Phe—L—NH—O—CH—CO—L—His—NH$_2$ (with CH$_2$Ph on CH) |
| 32 | t-BuCO—L—NH—O—CH—CO—L—NH—O—CH—CO—L—His—NH$_2$ (with CH$_2$Ph on each CH) |

Note: In Table 3, the meanings of the abbreviations are as follows:

| Abbreviations | Meanings |
|---|---|
| t-Bu | tert-butyl |
| Ph | phenyl |
| Phe | phenylalanine |
| MePhe | N-methylphenylalanine |

What we claimed is:

1. An imidazole-containing peptide of the formula:

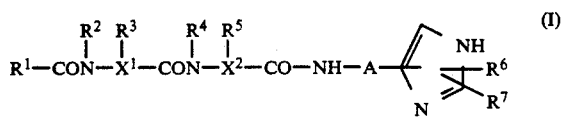

wherein $R^1$ is a branched $C_{3-6}$ alkyl group, a branched $C_{3-6}$ alkyloxy group or a phenyl-substituted lower alkyloxy group, $R^2$ and $R^4$ are the same or different and each is a hydrogen atom or a lower alkyl group, $R^3$ and $R^5$ are a phenyl-substituted lower alkyl group, $R^6$ is a hydrogen atom or a lower alkoxycarbonyl group, $R^7$ is hydrogen atom or a pyridyl-substituted lower alkylthio group, $X^1$ and $X^2$ are the same or different and each is

A is a lower alkylene group which may be substituted with a substituent selected from the group consisting of a lower alkoxycarbonyl group, hydroxymethyl group and a group of the formula —CON($R^8$)($R^9$), and $R^8$ and $R^9$ are hydrogen atoms, or a pharmaceutically acceptable salt thereof.

2. The compound claimed in claim 1, wherein $R^1$ is a phenyl-substituted $C_{1-4}$ alkyloxy group.

3. The compound claimed in claim 1, wherein $R^1$ is tert.-butyl, tert.-butyloxy or benzyloxy, $R^2$ and $R^4$ are hydrogen atom or methyl, $R^3$ and $R^5$ are benzyl or phenethyl, $R^6$ is hydrogen atom or methoxycarbonyl, $R^7$ is hydrogen atom, 2-pyridylmethylthio or 3-pyridylmethylthio, and A is methylene, ethylene, methoxycarbonylethylene, hydroxymethylethylene or carbamoylethylene.

4. The compound claimed in claim 3, wherein $R^1$ is tert.-butyl or tert.-butyloxy, and $R^3$ and $R^5$ are benzyl.

5. A pharmaceutical composition which comprises as an active ingredient an effective amount of the compound as set forth in claim 1, 2, 3 or 4 in admixture with a pharmaceutically acceptable carrier or diluent.

6. A pharmaceutical composition which comprises as an active ingredient an effective amount of the compound as set forth in claim 3 in admixture with a pharmaceutically acceptable carrier or diluent.

7. A pharmaceutical composition which comprises as an active ingredient an effective amount of the compound as set forth in claim 4 in admixture with a pharmaceutically acceptable carrier or diluent.

* * * * *